(12) United States Patent
Yoshikubo et al.

(10) Patent No.: US 6,232,448 B1
(45) Date of Patent: May 15, 2001

(54) IMMUNOLOGICAL MATERIALS AND METHODS FOR DETECTING DIHYDROPYRIMIDINE DEHYDROGENASE

(75) Inventors: Takashi Yoshikubo; Masami Hasegawa, both of Yokohama (JP)

(73) Assignee: Roche Diagnostics Corporation, Indianapolis, IN (US)

( * ) Notice: Subject to any disclaimer, the term of this patent is extended or adjusted under 35 U.S.C. 154(b) by 0 days.

(21) Appl. No.: 09/138,103

(22) Filed: Aug. 21, 1998

(30) Foreign Application Priority Data

Aug. 22, 1997 (EP) .................................. 97114630

(51) Int. Cl.[7] .................................. L07K 16/40
(52) U.S. Cl. .................. 530/388.26; 530/387.1; 530/388.1; 530/388.85; 435/326; 435/338; 435/344.1
(58) Field of Search .............. 530/387.1, 388.1, 530/388.85, 391.1, 391.3, 388.26; 435/326, 338, 344.1, 7.94, 7.1, 7.4; 424/146.1

(56) References Cited

FOREIGN PATENT DOCUMENTS

WO 95/28489 * 10/1995 (WO).

OTHER PUBLICATIONS

M. Iigo et al., Biochemical Pharmacology, vol. 38, No. 12, pp. 1885–1889 (1989).
G. Milano et al., Pharmacogenetics, vol. 4, pp. 301–306 (1994).
R. Diasio et al., Journal of Clinical Oncology, vol. 12, No. 11, pp. 2239–2242 (1994).
P. Fernandez–Salguero et al., Biochemical Pharmacology, vol. 50, No. 7, pp. 1015–1020 (1995).
A. Gennip et al., Advances in Experimental Medicine and Biology, vol. 253A, pp. 111–118 (1989).
J. Sommadossi et al., The Journal of Biological Chemistry, vol. 257, No. 14, pp. 8171–8176 (1982).
E. Harlow et al., Antibodies: A Laboratory Manual, Chapter 5, pp. 78–81 (1988).
Z. Lu et al., The Journal of Biological Chemistry, vol. 267, No. 24, pp. 17102–17109 (1992).
H. Yokota et al., The Journal of Biological Chemistry, vol. 269, No. 37, pp. 23192–23196 (1994).
P. Chomczynski et al., Analytical Biochemistry, vol. 162, pp. 156–159 (1987).
M. Nishida et al., Biol. Pharm. Bull., vol. 19, No. 11, pp. 1407–1411 (1996).
Paul, Fundamental Immunology, chapter 8, p. 242, 1993.*
Marglin et al, Ann Rev Biochem. vol. 39, pp 841–866, 1970.*
Lerner, Nature 299:592–596, 1982.*
Galfle et al, Methods in enzymology 73:1–46, 1981.*
Greenspan et al., Nature Biotechnology 17:936–937, 1999.*
Knight, Biotechnology 7:35–40, 1989.*

* cited by examiner

*Primary Examiner*—Sheela Huff
*Assistant Examiner*—Larry R. Helms
(74) *Attorney, Agent, or Firm*—Gibbons, Del Deo, Dolan, Griffinger & Vecchione

(57) ABSTRACT

Monoclonal antibodies against dihydropyrimidine dehydrogenase are disclosed. Immunologic assays using the monoclonal antibodies are also disclosed.

4 Claims, 7 Drawing Sheets

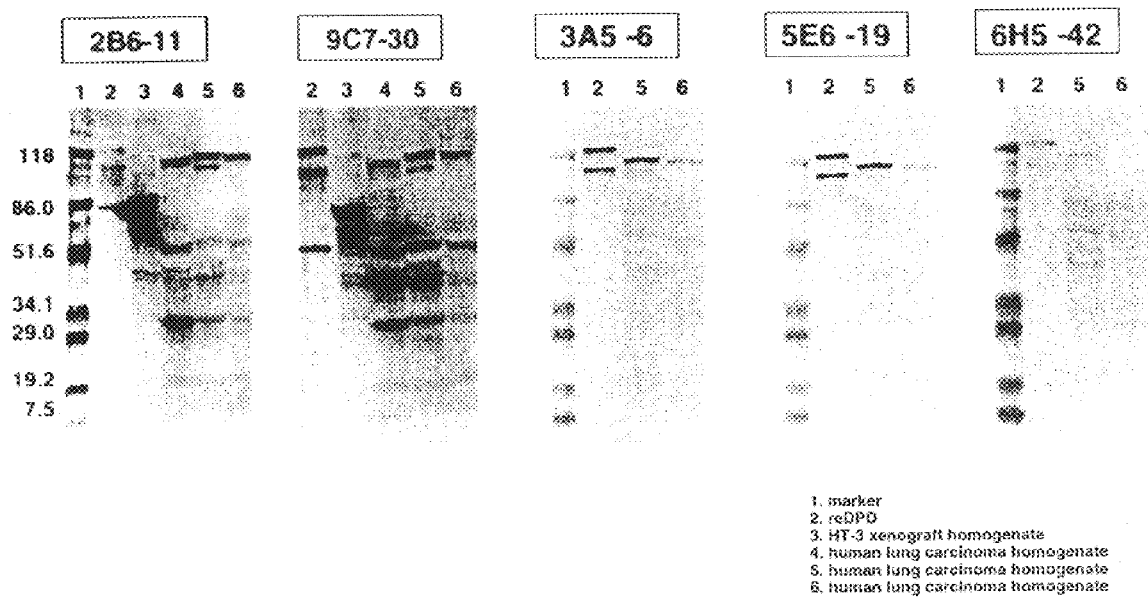

DPD (pmol/min/ml)

(o) : Tumor Tissue
(●) : Normal Tissue (a)

(b)

IMMUNOLOGICAL MATERIALS AND METHODS FOR DETECTING DIHYDROPYRIMIDINE DEHYDROGENASE

BACKGROUND OF THE INVENTION

The present invention relates to immunological materials and methods useful for the determination of dihydropyrimidine dehydrogenase (DPD) in biological samples.

Dihydropyrimidine dehydrogenase (DPD) is an enzyme which catalyzes the reduction of pyrimidines to 5,6-dihydropyrimidine, where the resulting catabolites, dihydrouracil and dihydrothymine, are further catabolized to β-alanine or β-aminoisobutylic acid, respectively.

DPD is also known to catalyze the reducing reactions of 5-fluorouracil (5-FU) and various catabolites from pyrimidine analogues and derivatives, which are widely utilized as antitumor medicines, such as 2'-deoxy-5-fluorouridine (2'-dFUrd), 5'-deoxy-5-fluorouridine (5'-dFUrd, doxifluridine), and the like. It has been reported that the DPD level in biological samples of individuals suffering from tumor is an interesting marker of the therapeutic efficacy of antitumor medicaments in the series of 5-fluorouracil derivatives (see e.g. Iigo et al., 1969, Biochem. Pharmacol., 38, 1885–1889).

Deficiency in DPD is known to be responsible for the toxicity of the metabolites of pyrimidine antitumor medicines, which results in life-threatening condition during chemotherapy (Milano, G. and Etienne, 1988, M.C., Pharmacogenetics, 4, 301–306). Recently it was found that the disorder of DPD deficiency is more frequent than initially thought (Diasio and Lu, 1994, J. Clin. Oncol., 12, 2239–2242). It is thus important to identify patients with DPD deficiency.

There is therefore a need for a sensitive and reliable assay for the determination of the DPD level in biological samples.

Several methodologies for such assays have been described. Femandez-Salguero et al. reported a thin layer chromatography (TLC) procedure for the determination of DPD activity in human peripheral lymphocytes (Femandez-Salguero et al., 1995, Biochem. Pharm. 50, 1015–1020). The assay uses radiolabeled uracil as a substrate. However, a method which uses a radiolabel is obviously not adapted to routine diagnosis in hospitals. Furthermore, such a TLC method is time-consuming.

Other assay methods utilizing HPLC have been also described, e.g. by van Gennip et al., 1982, Adv. Exp. Med. Biol., 253A: 111–118, and Sommadossi et al., 1982, J. Biol. Chem., 257: 8171–8176. Those methods are based on the measurement of enzyme activity by the determination of the sum of various catabolites of 5-FU using reverse phase HPLC. Such methods are cumbersome and time-consuming.

The problem addressed by the present invention is to find materials and methods for the determination of DPD level that do not have the drawbacks of the above known methods, and that provide a simple and speedy assay for routine use in hospitals.

SUMMARY OF THE INVENTION

The above problem is solved by the invention as defined in the appended claims.

The present invention provides a monoclonal antibody specifically recognizing dihydropyrimidine dehydrogenase (DPD), and particularly human dihydropyrimidine dehydrogenase.

The above monoclonal antibody is suitably a monoclonal antibody that shows strong reactivity to a homogenate from human tumor cell line HT-3 (ATCC HTB-32), but a low reactivity or no reactivity to a homogenate from human tumor cell line MCF-7 (ATCC HTB-22).

The above monoclonal antibody is a monoclonal antibody that shows a high specificity for DPD.

Suitably the immunoprecipitate obtained with a homogenate from human tumor cell line HT-3 (ATCC HTB-32) will show a single band when analyzed by SDS-PAGE.

The monoclonal antibody can suitably be produced by a hybridoma cell line selected from the group consisting of hybridoma cell lines 2B6-11-1, 9C7-30-1, 5E6-19-1, 3A5-6-1 (FERM BP-6015), 6H5-42-1, 4B9-12-1 (FERM BP-6016), 2E2-B3-1-3 (FERM BP-6014) and 3B12-B1-56-1-2. Preferably the monoclonal antibody is one produced by a hybridoma cell line chosen among 3A5-6-1 (FERM BP-6015), 4B9-12-1 (FERM BP-6016), 2E2-B3-1-3 (FERM BP-6014).

The monoclonal antibody can also be any monoclona antibody that binds to DPD in an equivalent manner as a monoclonal antibody produced by one of the above cell lines, i.e. a monoclonal antibody which binds to the same epitope as a monoclonal antibody produced by one of the above cell lines or crossreacts strongly with a monoclonal antibody produced by one of the above cell lines.

The invention also concerns a hybridoma cell line producing the above defined monoclonal antibody.

That hybridoma cell line is suitably chosen from the group consisting of hybridoma cell lines 2B6-11-1, 9C7-30-1, 5E6-19-1, 3A5-6-1 (FERM BP-6015), 6H5-42-1, 4B9-12-1 (FERM BP-6016), 2E2-B3-1-3 (FERM BP-6014) and 3B12-B1-56-1-2, and preferably a hybridoma cell line chosen among 3A5-6-1 (FERM BP-6015), 4B9-12-1 (FERM BP-6016), 2E2-B3-1-3 (FERM BP-6014).

The present invention also relates to a pair of monoclonal antibodies which is useful for the qualitative and/or quantitative detection of DPD, wherein the pair comprises a first monoclonal antibody specifically recognizing dihydropyrimidine dehydrogenase and a second monoclonal antibody specifically recognizing dihydropyrimidine dehydrogenase, wherein the first monoclonal antibody and the second monoclonal antibody recognize different epitopes from one another.

Such a pair of monoclonal antibodies can include as first monoclonal antibody, a monoclonal antibody selected from the group consisting of Mab-3A5-6-1, Mab-6H5-42-1 and Mab-3B12-B1-56-1-2, and as second monoclonal antibody, a monoclonal antibody selected from the group consisting of Mab-4B9-12-1, Mab-2E2-B3-1-3, Mab-9C7-30-1, Mab-2B6-11 -1 and Mab-5E6-19-1.

Preferably the first monoclonal antibody is Mab-3A5-6-1, and the second monoclonal antibody is Mab-4B9-12-1 or Mab-2E2-B3-1-3.

Further the present invention relates to kit for the detection and/or determination of the amount of dihydropyriridine dehydrogenase in a biological sample which comprises (a) at least one monoclonal antibody as defined above, and (b) a label for qualitatively and/or quantitatively detecting the immunoconjugate of the monoclonal antibody and dihydropyrimidine dehydrogenase.

Preferably that kit comprises a pair of monoclonal antibodies and a label as defined above.

In another aspect, the invention relates to an immunoassay method for detecting and/or determining the amount of dihydropyrimidine dehydrogenase in a biological sample which comprises (a) treating the sample with at least one monoclonal antibody as defined above, so to produce an immunoconjugate between that antibody and dihydropyrimidine dehydrogenase, and (b) qualitatively or quantitatively detecting the said immunoconjugate with the aid of a label.

The immunoassay can be of any immunoassay format known in the art of immunoassays (see e.g. M. Ferencik, 1993, in "Handbook of Immunochemistry", published by Chapman & Hall, London, UK). In particular it can be one-point binding assay, e.g. an immunoprecipitation method, or a two-point binding assay (sandwich assay), e.g. an ELISA. A two-point binding assay will preferably use a pair of monoclonal antibodies as defined above.

In a further aspect the invention relates to a method for the determination of the DPD deficiency state of a patient which comprises; (a) treating a biological sample from the patient with a monoclonal antibody as defined above, and (b) quantitatively detecting the immunoconjugate of the monoclonal antibody and dihydropyrimidine dehydrogenase.

In another aspect the invention concerns a method for estimating the susceptibility of patients suffering from cancer to the treatment with antitumor medicaments in the series of 5-fluorouracil (5-FU) derivatives, which comprises (a) treating a biological sample from the patient with a monoclonal antibody as defined above, (b) quantitatively detecting the immunoconjugate of the monoclonal antibody and human dihydropyrimidine dehydrogenase, so as to determine the level of dihydropyrimidine dehydrogenase in the biological sample from the patient to obtain a measure of susceptibility.

The above method enables the physician, by comparing that measured level of DPD for a patient to that of a reference set of patients, to predict the efficacy and toxicity of the above medicaments.

In further aspect the invention concerns a method for estimating the susceptibility of patients suffering from cancer to the treatment with antitumor medicaments in the series of 5-fluorouracil (5-FU) derivatives, which comprises (a) treating a biological sample from the patient with a monoclonal antibody as defined above, (b) quantitatively detecting the immunoconjugate of the monoclonal antibody human and dihydropyrimidine dehydrogenase, so as to determine the level of dihydropyrimidine dehydrogenase in the biological sample from the patient, (c) determining the level of pyrimidine nucleoside phosphorylase in the said biological sample from the said patient, and (d) calculating the ratio of the level of pyrimidine nucleoside phosphorylase and the level of dihydropyrimidine dehydrogenase to obtain a measure of susceptibility.

The above method enables the physician, by comparing that calculated ratio of the level of pyrimidine nucleoside phosphorylase and the level of dihydropyrimidine dehydrogenase for a patient and that of a reference set of patients, to predict the efficacy of the above medicaments.

BRIEF DESCRIPTION OF THE FIGURES

In FIG. 1, lane 1 is molecular weight marker, lane 2 is GST protein per se, lane 3 is GST-DPD fusion protein.

FIG. 3 shows that the ELISA of the present invention enabled the determination of the DPD activity over the range from, about 2.5 to about 170 pmol/minute/ml.

FIGS. 6-1(a) and (b) show the results of SDS-PAGE, where (a) is for the supernatants and (b) is the bead eluates of the immunoprecipitates. FIGS. 6-2(a), (b) and (c) show results of Western blotting, where (a) is the result obtained from the supernatant detected using anti DPD-1 polypeptide antibody, (b) is the result from the elutions from the immunoprecipitates detected by using anti DPD-1 polypeptide antibody, and (c) show the result from the same elutions as (b) in which the monoclonal antibody 3A5-6-1 of the present invention was used for the detection. The respective lanes correspond to the results of the immunoprecipitation assay using the following samples: lane 1: mouse IgG 1; lane 2: 2B6-11-1; lane 3: 2E2-B3-1-3; lane: 4B9-12-1; and lane 5: 9C7-30-1. The lane c in FIG. 6-2(b) is the run of homogenate of HT-3 as a positive control.

DETAILED DESCRIPTION OF THE INVENTION

Preparation of Monoclonal Antibodies

Figure 1:
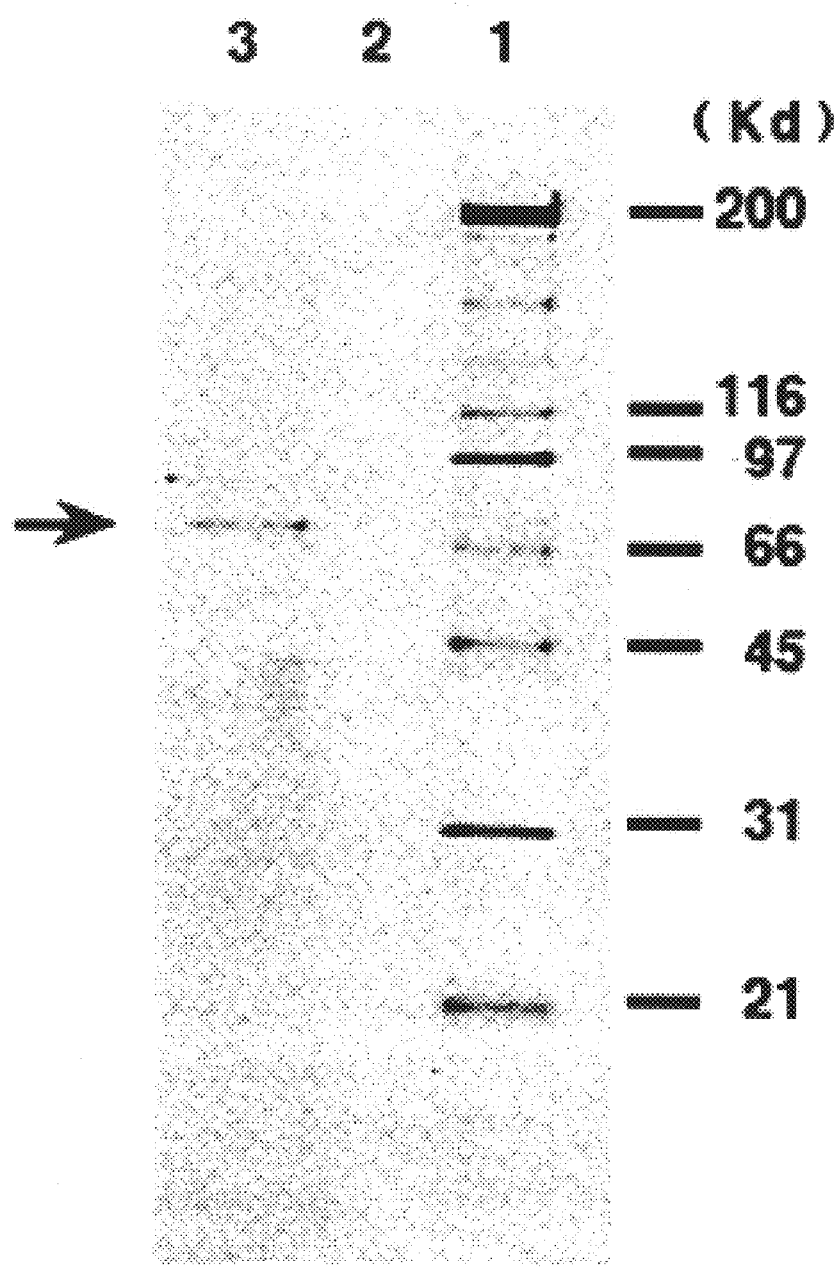
FIG. 1 illustrates the confirmation of the antigenicity of the recombinant GST-DPD fusion proteins produced in Example 1 by Western Blotting with anti-DPD Peptide 2 antibody.

The methodology for the production of a monoclonal antibody to a specific antigen is well known in the art and described e.g. by Harlow et al., 1988, Section 6 of "Antibodies: a Laboratory Manual", Cold Spring Harbor Press, New York, USA.

Hybridoma cell lines which produce monoclonal antibodies recognizing specifically DPD are first established. For this purpose, an experimental animal is immunized with the DPD protein or fragments thereof as antigens. The experimental animal can be of any species possessing immunocompetent cells such as lymphocytes and spleen cells apt to be used to establish a hybridoma cell line. Suitable species are for instance mouse, rat, rabbit and goat. Mouse or rat is particularly convenient. The antigen may be the DPD protein per se or fragments thereof including a mixture of such fragments. The DPD protein or fragments thereof used as antigens can be obtained either by isolating the protein from a natural source or by producing with the aid of recombinant technology. The DPD protein can be obtained from natural source, such as liver tissues, preferably from human, by the isolation method as already reported e.g. by Lu et al. in J. Biol. Chem. 267, 17102–17105, 1992.

Genetic recombinant technology provides a convenient means for the preparation of recombinant antigens. The information of nucleotide sequence of human DPD is available from GenBank™/EMBL Data Bank with accession number U09179 (see Yokota, H. et al., 1994, J. Biol. Chem. 269, pp. 23192–23196). The nucleotide sequence of human DPD and the amino acid sequence deduced therefrom are set forth in the sequence listing hereinbelow as SEQ ID NO: 1 and SEQ ID NO: 2, respectively. Based on this sequence information, a recombinant DPD protein or a fragment therof can be produced using either a synthetic DNA or a cloned DPD gene with the aid of conventional expression systems for recombinant gene. When cloning is desired, the cloning strategy can based on any nucleic acid amplification method e.g. using polymerase chain reaction (PCR), ligase chain reaction (LCR), transcription amplification or self-sustained sequence replication. Polymerase chain reaction (PCR) is particularly reliable and convenient. PCR cloning strategy can provide the full nucleotide sequence of the DPD gene or the partial nucleotide sequence of that gene. It is shown in the Examples that a fragment of DPD in a form of a fusion protein with GST protein is an effective antigen for immunizing an animal.

The amino acid sequence as described in SEQ ID NO: 2 provides useful information for the chemical synthesis of DPD fragment(s). Such synthetic peptides are also useful as an antigen for the present invention. The antigens prepared by either of the above methods can be evaluated for their antigenicity by Western blotting.

By the injection of the said antigen into a mouse, rat, sheep, rabbit or the like, monoclonal antibodies of the present invention can be prepared by recovering antibody producing cells from such an immunized animal and immortalizing the said cells. The immunization of the animals with the above antigen can be conducted by procedures well known in the art, described e.g. by the above reference of Harlow et al. The immortalization provides hybridoma cell lines producing monoclonal antibodies, and may be conducted in conventional fashion like fusion of the antibody producing cells with myeloma cells.

Supernatants of the culture of such hybridomas are screened for monoclonal antibodies by conventional procedure like dot-immunobinding assays, such as Western blotting, or radio-immunoassays, enzyme immunoassays or the like.

Monoclonal antibodies can be purified from hybridoma supernatants by conventional chromatographic procedures, for example ion exchange chromatography, affinity chromatography on protein G or protein A, HPLC or the like.

For the production of large quantities of monoclonal antibodies in accordance with methods well-known in the art, hybridomas secreting the desired antibody can be injected intraperitoneally into mice which have been pretreated with pristane before injection. Up to around 100 mg of a monoclonal antibody can be produced by such ascites tumors in one mouse. Monoclonal antibodies can be purified for example from ascites fluid produced by such tumors as described in Example 2.

Monoclonal antibodies can be characterized according to their subclass by known methods such as Ouchterlony immunodiffusion, or using a commercially available test kit, such as Mouse Mono Ab-ID EIA Kit (Zymed, San Francisco, Calif., USA). In the present invention, the subclass of the particular monoclonal antibodies from the hybridoma cell lines prepared in Example 2 were determined to be Mab-2B6-11-1 (IgG1, κ), Mab-9C7-30-1 (IgG1, κ), Mab-4B9-12-1 (IgG1, κ), Mab-2E2-B3-1-3 (IgG1, κ), MabMab-5E6-19-1 (IgG3, κ), Mab-3A5-6-1 (IgM, κ), Mab-6H5-42-1 (IgM, κ), 3B12-B1-56-1-2 (IgM, κ), respectively.

The hybridoma cell lines according to the invention designated as 4B9-12-1, 3A5 -6-1 and 2E2-B3-1-3 are particularly useful for the production of the monoclonal antibodies of the present invention, particularly for multisite binding assays. Those cell lines were deposited at the National Institute of Bioscience and Human-Technology (NIBHT), Agency of Industrial Science and Technology M.I.T.I., 1-1, Higashi, Tsukba, Ibaraki, 305 Japan on Jul. 8, 1997 in accordance with the Budapest Treaty with the following accession numbers: FERM BP-6014 for 2E2-B3-1-3, FERM BP-6015 for 3A5-6-1 and FERM BP-6016 for 4B9-12-1.

The monoclonal antibodies of the present invention can be used for the immunoaffinity purification of DPD. Such antibodies can to that end be linked to solid supports by methods well-known in the art, for example by covalent binding to CNBr activated agarose, such as Sepharose, or the like.

Furthermore, the monoclonal antibodies of the present invention can also be used as diagnostic tools for the determination of DPD level in a biological samples which may be tumor tissues of human patients. For such use, monoclonal antibodies may be coupled to a fluorescent dye, a color producing substance, like an enzyme (enzyme linked immunosorbent assay: ELISA) or a label conventionally used in the art, such as biotin.

For the purpose of investigating the performance of the assay format which can be constructed by the use of monoclonal antibodies of the present invention, the following conventional assay, which utilizes radioisotope, may be used.

Assay Method of DPD Enzymatic Activity

The enzyme activity of DPD can be determined by measuring the sum of the 5-FU catabolites, i.e. dihydrofluorouracil, α-fluoro-β-ureidopropionate, and α-fluoro-β-alanine, formed from [6-$^{14}$C]5-FU. The following procedure can be applied to the above assay:

The standard reaction mixture contains 10 mM potassium phosphate (pH 8.0), 0.5 mM EDTA, 0.5 mM 2-mercaptoethanol, 1 mM dithiothreitol, 2.5 mM MgCl$_2$, 250 μM NADPH, 25 μM [6-$^{14}$C]5-FU (56 mCi/mmol), and 25 μl crude enzyme (final protein concentration: 1 mg/ml) in a total volume of 50 μl. The reaction is carried out at 37° C. for 30 minutes and then terminated by immersing the reaction tubes (0.5 ml Eppendorf tubes) in a boiling water bath for 30 minutes. The reaction tubes are frozen at −20° C. for at least 20 minutes before further manipulations are undertaken. Proteins are removed by centrifugation, and then 10 μl of the supernatant fluid are spotted on silica gel TLC sheets (MERCK 5735) which are prespotted with 5 μl of authentic markers mixture of 10 mM 5-FU, 50 mM dihydrouracil, 20 mM β-ureidopropionate, 10 mM α-fluoro-β-alanine, and 50 mM urea. The spots are developed in a solvent system of a mixture of ethylacetate/isopropanol/H$_2$O (65:23:12, v/v/v). These markers developed are identified by the methods of Naguib et al., 1985, Cancer Res. 45, 5405. The radioactivity of the spots identified as the 5-FU catabolites can be detected by BAS 1000 System (Fuji Film). DPD activity is expressed as pmol 5-FU converted/mg protein/minute.

Enzyme Linked Immunosorbent Assay (ELISA)

As typical application of the monoclonal antibodies of the present invention in immunological quantitative assays, a one-point binding method and two-point binding method (so called sandwich assay) are contemplated. It can generally be said that two-point binding methods are advantageous in achieving higher accuracy and higher sensitivity. An ELISA using a pair of monoclonal antibodies as defined above proved to be a sensitive and quick assay format (see Example 3).

That ELISA can be performed by immobilizing one of the antibodies onto a solid carrier, subjecting thus immobilized antibody to contact with a sample suspected to contain DPD to form a DPD-antibody conjugate, reacting this conjugate with the other monoclonal antibody to forma DPD sandwiched conjugate, i.e. antibody-DPD-antibody, and labeling the latter conjugate, for example by HRP labeled rat antimouse immunoglobulin antibody, to detect the conjugate. In case that HRP label is used, detection can be performed by coloring reaction using, for example TMB microwell peroxidase kit system (KPL) which contains TMB and $H_2O_2$ as a substrate developing color in the enzymatic reaction catalyzed by HRP. As a label for detection, the rat antimouse immunoglobulin antibody may have any conventional label, such as biotin, an enzyme, a radioisotope and the like. Alternatively, the monoclonal antibody in mobile phase may be labeled with HRP, biotin, radioisotope, latex particle and the like.

As shown in Example 3, a high sensitivity of the ELISA can be attained using the above defined pair of monoclonal antibodies. That high sensitivity makes the assay useful for determining the DPD level in biological samples from human body, even in case of a low level of DPD, as in the above described condition of DPD deficiency.

Immunopecipitation

The monoclonal antibodies according to the invention are also useful for isolation and determination of the DPD protein by an immunoprecipitation method. The methodology of immunoprecipitation itself is well known in the art. Using a monoclonal antibody as defined above it provides the specific separation of the target antigen (DPD) from a complex sample due to the high binding specificity of that monoclonal antibody.

One of the typical precipitating agents which can be used, is Protein G-Sepharose 4B, wherein Protein G capable of binding to the Fc region of mouse immunoglobulin is immobilized on the surface of Sepharose 4B beads. This agent forms a complex of DPD-antibody-Protein G-Sepharose beads, when DPD is present, and the complex can be separated by centrifugation. From the collected precipitate of the complex, the antigen (DPD) and antibody can be dissociated under an acidic condition, such as in a glycine-HCl-buffer, pH 3.0. Thus separated DPD can be readily isolated from immunoglobulin with the aid of gel filtration. Such complex to which DPD is bound is useful not only for the isolation of this enzyme but also for the quantification of the enzyme. Thus the monoclonal antibodies of the present invention are potent tools for the isolation and determination of DPD from a complex biological samples as is shown in Example 6 below.

Antibody Capture Assay

The monoclonal antibodies of the present invention are also useful in the antibody capture assay. In this assay format, the monoclonal antibody is immobilized on surfaces of an appropriate container, such as the wells of microtiter plate. Immobilization is performed by a conventional method known in the art. When a sample containing DPD is added to such wells, the DPD peptide is captured by the immobilized monoclonal antibody of the present invention. After washing the wells a solution containing the substrate of DPD is added. Thus the detection system of enzymatic product will provide a determination means of DPD activity. This assay format will be useful to determine whether the captured DPD has its intact enzymatic action, since the patients carrying genetic defects on the DPD gene may have mutated DPD proteins which lack enzymatic activity.

Alternatively, after DPD is captured by the immobilized monoclonal antibody, such immuno complex is washed and then DPD polypeptide is eluted by an appropriate buffer solution, for example under acidic condition. This manipulation also provides a purified DPD preparation.

Abbreviatios

The following abbreviations will be used hereinbelow.
DPD: dihydropyrimidine dehydrogenase
PyNPase: pyrimidine nucleoside phosphorylase
GST: glutathione S-transferase
IPTG: isopropyl β-D-thiogalactopyranoside
KLH: keyhole limpet hemocyanin
5-FU: 5-fluorouracil
CFA: complete Freund's adjuvant
IFA: incomplete Freund's adjuvant
EIA: enzyme immuno assay
ELISA: enzyme linked immunosorbent assay
TLC: thin layer chromatography
PBS: phosphate buffered saline
PCR: polymerase chain reaction
TMB: tetramethylbenzidine
(TMB: kit contains 3,3',5,5'-tetramethylbenzidine and $H_2O_2$.)
TBS: Tris-buffered saline (20 mM Tris/50 mM NaCl, pH 7.4)
TTBS: TBS containing 0.05% TWEEN®-20

The present invention will be further illustrated by the following examples. The following description will be better understood by referring to the following FIGS. 1, 2, 3, 4, 5, 6-1 and 6-2.

EXAMPLE 1

Preparation of Antigens

As described previously, the nucleotide sequence of human DPD and the amino acid sequence deduced therefrom were reported by Yokota, H. et al., 1994, J. Biol. Chem., 269, (37) 23192–23196 (see SEQ ID NO: 1 and SEQ ID NO: 2). A fusion protein as an antigen was prepared based on the genetic information from the position 1770 to the position 3164 of SEQ ID NO: 1, which fusion protein was expressed as GST-DPD fusion protein with the aid of a host organism *E. coli* JM 109 transformed with the vector pGEX 4 T-3 carrying the said genetic information as described below.

1) Construction of a DPD Expression Vector

On the basis of the genetic information of the position 1770–3164 of SEQ ID NO: 1, three DNA primers were prepared for the purpose of cloning a segment of the DPD gene by polymerase chain reaction (PCR). Primer 1 (Eco RI linker+sense) was prepared as a 25-mer having a sequence consisting of an Eco RI linker (CGCGAATTC) at the 5'-end portion and a positive strand corresponding to nucleotides 1770–1785 of SEQ ID NO: 1.

Primer 1: 5'-CGCGAATTCTTTTGAAGCTGGAT-3'(SEQ ID NO: 3)

(1770 Eco RI linker+sense)

Primer 2 (Eco RI linker+antisense) was prepared as a 26-mer having a sequence consisting of an Eco RI linker at the 5'-end portion and a negative strand complementary to nucleotides 3148–3164 of SEQ ID NO: 1.

Primer 2: 5'-CGCGAATTCTCACCTTAACACAC (SEQ ID NO: 4)

(3164 Eco RI linker+antisense)

Primer 3 (antisense) was prepared as a 16-mer having a sequence complementary to the sequence corresponding to nucleotides 3495–3510 of SEQ ID NO: 1.

Primer 3: 5'-AATCAAATATGGAGCA-3' (SEQ ID NO: 5)

(3510 antisense)

Total RNA was prepared from human lung diploid cell line WI138 cell (ATCC CLL-75) by a conventional method using RNA Isolation Kit (Stratagene, La Jolla, Calif., USA) based on the acid guanidinium thiocyanate phenol chloroform extraction (AGPC) method (see e.g. Chomczynski, P. and Sacci, N., 1987, Anal. Biochem. 162, 156–159), and was subjected to reverse transcription reaction of reverse transcriptase RAV-2 using Primer 3 to obtain a cDNA preparation. In the reaction, 1 µg of the total RNA was subjected to the reverse transcription reaction in 20 µl of the reaction solution at 42° C. for 60 minutes, and after reverse transcriptase was denatured by heating at 95° C. for 5 minutes. The cDNA preparation thus obtained was kept at 4° C. until use in PCR amplification. The buffer solution used in the synthesis of the first strand cDNA contained 5 mM $MgCl_2$, 1 mM each of dGTP, dATP, dTTP and dCTP, RNase inhibitor, 20 units of reverse transcriptase RAV-2 and 0.75 µM of the primers.

Then this cDNA preparation was subjected to PCR amplification using Primers 1 and 2 and a commercial PCR kit, namely RT-PCR Kit (Takara Shuzo, Shiga, Japan), according to the instructions of use of the kit with the exception that DNA polymerase (3.5 units of pfu) was used instead of Taq polymerase on an apparatus for thermal cyclization (ZYMOREACTOR II, ATTO, Tokyo, Japan). The buffer solution for PCR amplification having a total volume of 100 µl, contained 2 mM $MgCl_2$, 0.2 mM each of dGTP, dATP, dTTP and dCTP, and each 0.4 µM of the primers. The PCR program was 32 cycles of 94° C. for 30 s, 55° C. for 1 minute, and 75° C. for 4 minutes. Thus amplified DPD cDNA fragments were isolated by agarose gel electrophoresis as a band corresponding to 1.4 kbp, and then purified using QIAEX11 gel extraction kit (QIAGEN, Hilden, Germany). The purified cDNA fragment was digested with Eco RI and the Eco RI fragment was inserted into the Eco RI site of the vector pGEX4T-3 (Pharmacia, Uppsala, Sweden) using DNA Ligation Kit (Takara Shuzo, Shiga, Japan) at 16° C. overnight. Thus obtained vector (hereafter referred to as pGEX4T-3-DPD) was able to express a GST-DPD fusion protein. The partial nucleotide sequence of the above insertion fragment was determined and confirmed to have the expected subsequence of the DPD gene.

2) Expression of GST-DPD Fusion Protein

E. coli JM109 (Toyobo, Osaka, Japan) was transformed with pGEX4T-3-DPD, and the transformant was cultivated in the medium of SOB (20 g/l bacto-tryptone, 5 g/l bacto-yeast extract, 0.5 g/l sodium chloride, 0.186 g/l potassium chloride and 0.95 g/l magnesium chloride; pH 7.0) containing 50 µg/ml of ampicillin at the temperature of 22° C. to express the fusion protein. The cells of the said E. coli transformant were treated by the addition of 0.5 mM IPTG (isopropyl β-D-thiogalactopyranoside) and were incubated at 22° C. for about 16 hours, and subsequently subjected to sonification in a buffered solution containing 1% TRITON®-X100, 1% sarcosyl, 10 mM DTT and 2 mM EDTA/PBS. The cell lysate was centrifuged, and the soluble fraction was applied to Glutathione-Sepharose 4B column (Pharmacia, Uppsala, Sweden). The adsorbed GST-DPD fusion protein was eluted by 10 mM of reduced glutathione. GST-DPD fusion protein was identified as an about 75 kDa protein on SDS-PAGE.

This fusion protein was confirmed by the reaction with an anti-DPD peptide antibody. For this purpose, two peptides of DPD, namely Peptide 1 (SEQ ID NO: 6) and Peptide 2 (SEQ ID NO: 7) were chemically synthesized based on the sequence described as SEQ ID NO: 2 and were coupled with KLH with the aid of the glutaralaldehyde method to obtain the antigens, as described e.g. by Harlow et al., 1988, in "Antibodies: a Laboratory Manual", Cold Spring Harbor Press, New York, USA, pp 78–79. The respective antigens in the amount of 200 µg were subcutaneously injected together with CFA to rabbits to immunize the animals, followed by booster doses of the same amount of the antigens with IFA. The antisera thus produced were treated through a KLH column (which is a column wherein KLH is immobilized on a carrier, namely Affigel-10, available from BioRad, Hercules, Calif., USA) to remove anti-KLH antibodies and then purified by applying to Protein G column (MAB Trap GII, Pharmacia, Uppsala, Sweden) or a peptide column and eluting with a buffer of 0.1M glycine-HCl, pH 3.0, followed by the neutralization with 1M Tris HCl buffer, pH 8.0 before use. The peptide column was prepared by coupling the above mentioned Peptide 1 or Peptide 2 with Affigel-15 (BioRad, Hercules, Calif., USA). Both of these anti-DPD Peptide 1 and anti-DPD Peptide 2 polyclonal antibodies were reactive with DPD from human and mouse liver in the Western blotting, and thus were utilized to confirm the production of GST-DPD fusion protein. As described above, it was confirmed that the transformant produced the said GST-DPD fusion protein by the Western blotting with anti-DPD Peptide 2 (see FIG. 1). In FIG. 1, lane 1 was molecular marker, lane 2 is GST protein per se, lane 3 is GST-DPD fusion protein. As seen in lane 3, the fusion protein was confirmed to be a protein of about 75 kDa.

EXAMPLE 2

Preparation of Anti-DPD Monoclonal Antibodies

1) Cell Fusion

GST-DPD fusion protein prepared in Example 1 (50 µg per an animal) together with CFA was intraperitoneally injected to Balb/c mice in a volume of 100 µl/mouse, followed by intraperitoneal booster doses of about 10 µg per animal of GST-DPD protein together with IFA twice after the interval of two weeks. Three days after the final immunization, the sensitized mice were sacrificed to remove spleens, and spleen cells were prepared. The spleen cells thus obtained were carefully washed with the serum free RPMI 1640 medium (Nikken Seibutu Igaku Kenkyusho, Kyoto, Japan) which was pre-warmed at about 37° C. The subsequent fusion procedures were performed at about 37° C. using pre-warmed reagents including buffer solution.

Mouse myeloma cell line P3×63 Ag8-U1 (purchased from Flow Laboratories Ltd, Irvine, UK) were also carefully washed with the serum free RPMI 1640 medium. The spleen cells (about $4×10^8$) were mixed with the mouse myeloma cell line P3×63 Ag8-U1 ($8×10^7$) in the ratio of 5:1, and cell fusion was performed as follows. The mixture of the cells were pelleted by centrifugation, and the medium was aspirated, then to the pellet of the mixture of the cells, 250 µl of 50% polyethylene glycol solution (PEG1500, Boehringer Mannheim) was added slowly over 1 minute with stirring the pellet by the tip of the micropipet; subsequently another 250 µl of 50% PEG solution was added slowly over 1 minute with stirring the pellet by the tip of the micropipet; and then the stirring by gentle rotation of the tube was continued for 2 minutes. To the cell fusion mixture, 50 ml of serum free RPMI 1640 medium (Nikken Seibutu Igaku Kenkyusho, Kyoto, Japan) was slowly added dropwise over 5 minutes and the cells were washed by centrifugation to remove PEG.

The mixture of the cells pelleted after the cell fusion were re-suspended in a medium of RPMI 1640 (Nikken Seibutu Igaku Kenkyusho, Kyoto, Japan) containing 10% of fetal calf serum (FCS), penicillin/streptomycin and 2ME, and pipetted in to the wells of 96 well plates which then were incubated under 5% of $CO_2$ at 37° C. On the days 2th, 4th and 7th during the incubation, the half amount of the medium of each well was substituted by HAT medium (prepared by adding HAT solution (Flow Laboratories Ltd, Irvine, UK) to 10% FCS containing RPMI medium) and the incubation was continued. From about 10th day of the incubation, botryoid colonies were formed in some of the wells, and finally proliferation of hybridoma cells were observed in 1056 wells.

2) Screening of Monoclonal Antibodies (2-1) Primary Screening

All the wells exhibiting the proliferation of hybridomas were investigated by ELISA (Enzyme Linked Immunosorbent Assay) for positive wells as follows. The wells of 96 well immunoplates (Maxisorp, Nunc, Roskilde, Denmark) were coated with GST-DPD fusion protein or GST using the amount of 50 μl/well of the solutions containing 1 μg/ml of either protein. Non-adsorbed protein was washed out with TTBS and the blocking was effected by the incubation with TBS containing 3% skim milk for 1 hour. The wells were washed with TTBS again and were added with 50 μl/well of the hybridoma culture supernatant, and kept at 37° C. for 1 hour. After the respective wells were washed with TFBS three times, horse radish peroxidase (HRP)-labeled goat anti-mouse immunoglobulin IgG+A+M (KPL) was added and the plates were kept at 37° C. for 1 hour. The respective wells were washed with TTBS four times, and then a substrate (TMB, Microwell Kit System, KPL) was added. After the termination of the reaction by the addition of 1M phosphoric acid, the absorption at 450 nm was measured using a microplate reader. The positive wells which reacted stronger with the coat of GST-DPD fusion protein than those of GST were gathered as the primary stock.

(2-2) Secondary Screening

To ensure the efficiency of the screening, the secondary screening was performed by using a recombinant protein having the full sequence DPD in Western blotting.

(A) Preparation of a Recombinant Protein Having the Full Sequence DPD

A recombinant protein of full sequence DPD was prepared by cloning the full length cDNA of DPD on the basis of RT-PCR cloning and by the expression of the gene inserted into an *E. coli* expression vector, pTrcHisA (Invitrogen, San Diego, USA), which method was essentially the same with that described in the case of the cloning and expression of GST-DPD fusion protein.

First, the first strand cDNA was prepared by the reverse transcription reaction of the human placenta and liver mRNA preparation (Clontech, Palo Alto, Calif., USA) using synthetic Primer 2 and RAV-2 reverse transcriptase. Then the PCR amplification of the targeted cDNA was performed using synthetic Primer 4 (EcoRI linker+sense, position 62; 5'-CGCGAATTCTCGAGACTGTAGGCACT-3', SEQ ID NO: 8) and Primer 2 and pfu DNA polymerase (Stratagene, Lajolla, Calif., USA). PCR was performed using Takara RT-PCR kit in accordance with the instructions of use on the thermal cycler ZYMOREACTOR 11 (ATTO, Tokyo, Japan) with 35 cycles of 94° C. for 30 s, 55° C. for 1 minute, and 75° C. for 8 minutes. Thus amplified cDNA fragments were separated by electrophoresis on 1% agarose gel and the DNA in the desired band was purified using the DNA purification kit QIAEX11 (QIAGEN, Hilden, Germany). The purified cDNA fragment was digested with Eco RI and subsequently subcloned into the Eco RI site of an expression vector, namely pTrcHisA (Invitrogen, San Diego, USA). Thus cloned DPD cDNA expressed a protein of about 120 kDa as a fusion protein of the full DPD with histidine tagged protein, which was used in the further screening.

(B) Screening

The above obtained recombinant DPD was subjected to electrophoresis on NPG-D520L gel (Pagel, ATTO, Tokyo, Japan) in accordance with Laemmli's methodology, and the protein was blotted onto PVDF membranes, (Immobilon, Millipore, Bedford, Mass., USA) using a semi-dry blotter (ATTO, Tokyo, Japan). The PVDF membranes onto which the DPD protein was blotted were blocked using TBS containing 3% of skim milk, and were washed with TTBS, and subsequently were submitted to the reaction with the culture supernatants of the hybridomas described in Example 1 on Screener Blotter Mini 28 (Sanplatec Corp., Japan) at room temperature for one hour. Then, after washing the PVDF membranes with TTBS, they were reacted with HRP-labeled goat anti-mouse IgG+A+M antibody (KPL) at room temperature for one hour. The membranes were washed with TTBS again and were subjected to a coloring reaction using Konica Immunostaining HRP-1000 (Konica, Tokyo, Japan). The colonies such as e.g. those designated 2B6, 9C7, 5E6, 3A5 and 6H5 which reacted strongly with the recombinant DPD of about 120 kDa were collected as the candidates. As used herein, a monoclonal antibody produced by a particular hybridoma, e.g. hybridoma 2B6, is designated by adding "Mab-" to the head of the name of the hybridoma, for instance Mab-2B6.

The above candidates were cloned by repeating the limiting dilution method twice or more to establish the hybridoma cell lines (including e.g. 2B6-11-1, 9C7-30-1, 5E6-19-1, 3A5-6-1 and 6H5-42-1). After the first limiting dilution, the specificity of the above monoclonal antibodies, i.e. Mab-2B6-11, Mab-9C7-30, Mab-5E6-19, Mab-3A5-6 and Mab-6H5-42 were evaluated by Western blotting using the samples containing DPD.

Figure 6:
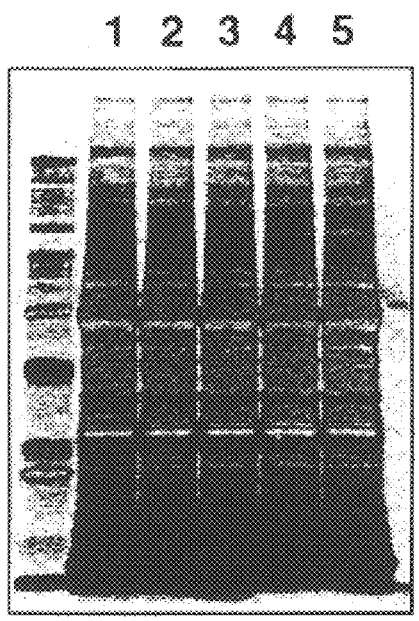
FIG. 6 illustrates the results of an immunoprecipitation assay using monoclonal antibodies according to the present invention as described in Example 6.
Figure 1:
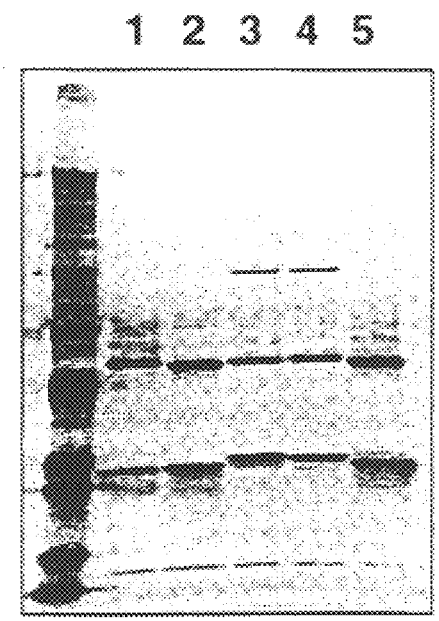
Figures 2, 6:
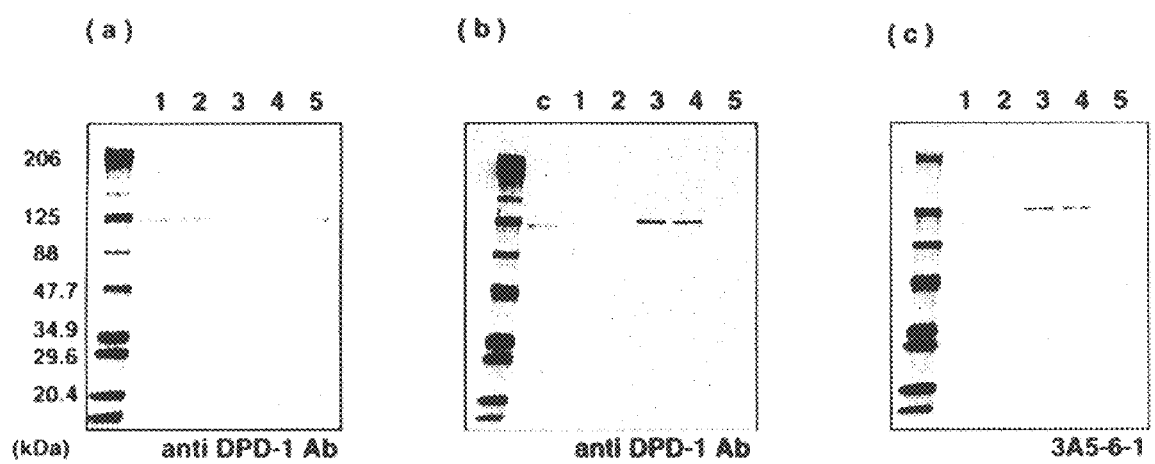
FIG. 2 illustrates the pattern of the Western Blot of the monoclonal antibodies of the present invention against human tissue homogenates containing DPD. In this Figure, lane 1 is for molecular weight marker; lane 2 is for recombinant DPD (rDPD); lane 3 is for a xenograft homogenate of a human tumor cell line, HT-3; and lanes 4, 5 and 6 are for the different human lung carcinoma homogenates, respectively.

FIG. 2 shows the results of the Western blotting for monoclonal antibodies produced by hybridoma cell lines 2B6-11, 9C7-30, 3A5-6-1, 5E6-19 and 6H5-42. As it is shown in this Figure, the resulting immunoconjugates with the antibodies and DPD were observed around the position of molecular weight of about 110–120 kDa.

The subclass of the monoclonal antibodies produced by the above hybridoma cell lines were investigated using Mouse Mono Ab-ID EIA Kit (Zymed, San Francisco, Calif., USA) and were determined as Mab-2B6-11-1 (IgG1, κ), Mab-9C7-30-1 (IgG1, κ), Mab-5E6-19-1 (IgG3, κ), Mab-3A5-6-1 (IgM, κ), Mab-6H5-42-1 (IgM, κ), respectively. It was confirmed that the above monoclonal antibodies were applicable to a sandwich ELISA for the detection of DPD. However, for the purpose of constructing a more sensitive ELISA system, a further screening was decided to be preferable since the concentration of DPD in tumor tissues was expected to be lower than in liver and high sensitivity will be desired so as to enable the distinction between a DPD-deficient level and normal level.

(2-3) Third Screening

Taking the monoclonal antibody of the hybridoma 3A5-6-1 as a representative, further monoclonal antibodies which recognize the different epitopes from that recognized by the antibody of Mab-3A5-6-1 and which would achieve a higher sensitivity in the detection of the native DPD in tissues than the above mentioned antibodies were screened.

The monoclonal antibody, Mab-3A5-6-1 was used to coat the wells of the plate using 50 µl/well in the concentration of 10 µg/ml, and after the unbound antibody was removed, the respective wells were blocked using TBS containing 3% of skim milk at room temperature for an hour. After washing with TTBS, the wells were reacted with 50 µl/well of a mouse liver homogenate in the concentration of about 2 mg/ml at room temperature for one hour. After washing with TTBS, the wells were reacted with the primary stock of the hybridoma culture supernatants in the amount of 50 µl/well at 37° C. for 1 hour. After washing again with TTBS, the wells were reacted with HRP labeled Rat anti-mouse IgG1 specific monoclonal antibody (Zymed, San Francisco, Calif., USA) at 37° C. for 1 hour. Subsequent to washing with TTBS, the wells were subjected to the color development with TMB microwell peroxidase kit system (KPL), then the reaction was stopped by the addition of 1M phosphoric acid and the absorption was measured at 450 nm using a microtiter plate reader.

The 22 wells with strong reaction were determined and the hybridomas of these wells were subjected to further screening in the same manner as described above by substituting the above mouse liver homogenate with the homogenates of human tumor cell lines, HT-3 and MCF-7. The said HT-3 had the DPD activity of 160 pmol/minute/mg protein and was detected as a single band around 110 kDa by Western blotting using rabbit anti-DPD-Peptide 1 or anti-Peptide 2 polyclonal antibody. On the other hand, whilst cell line MCF-7 had a DPD activity of about 1.6 pmol/minute/mg, it was not detected by the similar Western blotting. Thus the inventors selected the hybridomas (designated as 4B9 and 2E2) which reacted strongly with cell line HT-3 but not with cell line MCF-7. These hybridomas 4B9 and 2E2 were further subjected to the limiting dilution method twice or more and the hybridoma clones 4B9-12-1 and 2E2-B3-1-3 (the antibodies of which were determined as IgG1, κ) were established.

The monoclonal antibodies Mab-4B9-12-1 and Mab-2E2-B3-1-3 were confirmed in their specificity to the solubilized state DPD antigen by the immunoprecipitation.

(2-4) Purification of Monoclonal Antibodies

In general, once a hybridoma capable of producing a monoclonal antibody of the present invention is established, the production and purification of the monoclonal antibody can be conducted by any means for the production and purification of monoclonal antibodies known in the art. For example, the production of the monoclonal antibodies can be performed by cultivating the hybridoma cells in an appropriate culture medium, and recovering and purifying the antibodies from the culture. Alternatively the proliferation of the hybridoma cells can be conducted by planting the cells in peritoneal ascites of mice. The production and purification of the monoclonal antibodies are performed by a conventional method, exemplified as follows for specific monoclonal antibodies:

1) Mab-4B9-12-1

The hybridoma cell line 4B9-12-1 was cultured in a serum-free medium (PM 1000 Kit, Eiken, Tokyo, Japan) at the cell concentration of about $5 \times 10^5$/ml. The supernatant of the culture was collected and antibodies (IgG) was purified by applying the supernatant through HiTrap protein G column (Pharmacia, Uppsala, Sweden) as follows.

HiTrap protein G column was equilibrated with 20 mM phosphate buffer (pH 7.0) then the supernatant preparation was applied to the column. After washing the column with 20 mM phosphate buffered saline, the IgG fractions were eluted by 0.1M glycine-HCl buffer (pH 3.0). Thus collected elution was neutralized by 1M Tris-HCl (pH 9.0) and then dialyzed against PBS. The protein determination of the purified antibody fraction using BIO-RAD Dc Protein Assay kit (Biorad, Hercules, Calif., USA; the control was BSA) showed about 4 mg of antibody from 300 ml of the culture supernatant. The subclass of this monoclonal antibody was determined to be IgG1, κ.

2) Mab-3 A-6-1

One week after the injection of 0.5 ml of pristane (Sigma, St. Louis, Mo., USA) intraperitoneally to mice, $5 \times 10^6$ of hybridoma 3A5-6-1 cells were inoculated in abdominal cavity of the animals by injection. After two weeks, the ascites were collected from the animals, centrifuged and filtered through 0.8 µm membrane filter. The purification of antibodies (IgM) was performed by using ImmunoPure IgM Purification Kit (Pierce, Rockford, Ill., USA). To 0.5 ml of ascites, 0.5 ml of InmnunoPure IgM binding buffer was added and the mixture was applied to ImmunoPure Immobilized MBP column. After washing the column with ImmunoPure IgM binding Buffer, the antibodies were eluted with ImmunoPure IgM elution buffer, and the fraction of the antibodies were dialyzed against PBS. The protein determination using BSA as the control revealed that about 2 mg of antibodies (IgM) was obtained from about 0.5 ml of the ascites.

EXAMPLE 3

ELISA Using the Monoclonal Antibodies of the Present Invention

As immunological quantitative assays, one point binding methods and two points binding methods (so called sandwich assay) are well known in the art. It can generally be said that two point binding methods are advantageous in achieving higher accuracy and higher sensitivity. The monoclonal antibodies obtained in the above Example 2 were used to construct sandwich ELISA assay systems as described below:

(a) Coating of the First Antibody

A solution of Mab-4B9-12-1 was prepared using PBS (pH 7.4) in the concentration of 10 µg/ml and 50 µl of this solution was added to each of the wells of 96-well immunoplates (Maxisorp, Nunc, Roskilde, Denmark), and the wells were sealed by a membrane sealant and incubated at 4° C. overnight to immobilize the antibody (in this Example, the plates were sealed during incubation).

After recovering the unbound antibody, the wells were washed with TTBS and then blocked by incubating with TBS containing 3% of skim milk at room temperature for 3 hours.

(b) Application of Samples

As a standard sample containing DPD, HT-3 xenograft homogenate was prepared in the concentration of 2 mg/ml. A serial dilution of the homogenate was prepared in TBS containing 0.3% skim milk, and 50 µl of the samples were added to the respective wells, and then the immunoplate was incubated at 37° C. for 2 hours.

(c) Reaction With the Second Antibody

After washing the wells with TTBS, the second antibody solution which contained 2 µg/ml of Mab-3A5-6-1 in TBS containing 3% skim milk was added to each well in a volume of 50 µ, and the immunoplate was incubated at 37° C. for 1 hour. By this treatment, an immunoconjugate of [Mab4B9-12-1]-[DPD]-[Mab-3A5-6-1] in which DPD was sandwiched between the two monoclonal antibodies was produced, when DPD was present in the above samples.

(d) Labeling

For the purpose of detecting the conjugate, HRP labeled rat anti-mouse IgM antibody (Zymed, San Francisco, Calif., USA) was used to label the conjugate. This commercially available HRP-labeled antibody was used after diluting 1000 times with TBS containing 3% skim milk.

The wells of the immunoplate were washed with TTBS and were added with 50 µl of the above HRP-labeled antibody, and the plate was incubated 37° C. for 1 hour.

(e) Detection

After washing the wells, the coloring reaction was conducted by using TMB microwell peroxidase kit system (KPL) which contained TMB and $H_2O_2$ as a substrate developing color in the enzymatic reaction catalyzed by HRP. The substrate solution was added to the respective wells, and after the reaction was stopped by addition of 1M phosphoric acid, the absorption of the wells were measured by a microplate reader (BioRad, Hercules, Calif., USA) at 450 nm.

Figure 3:
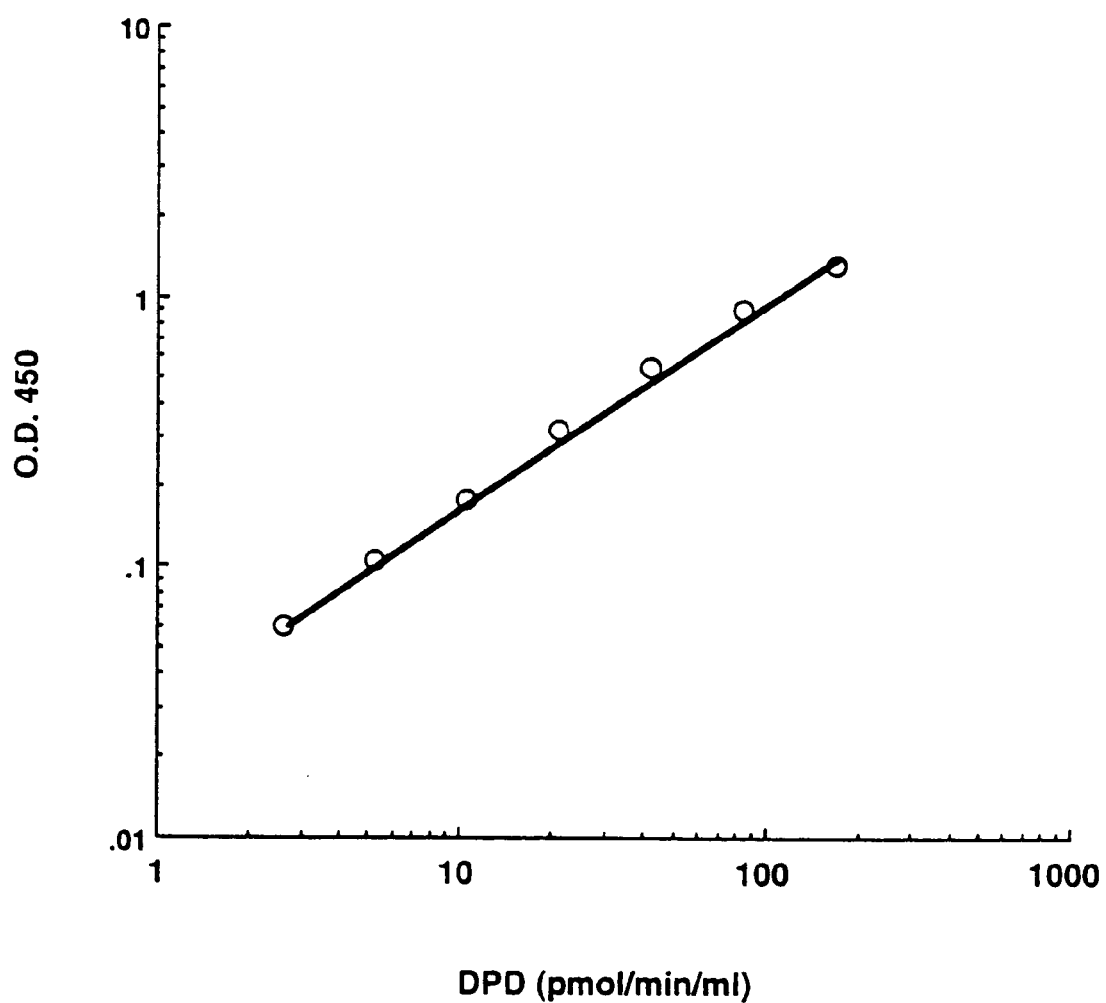
FIG. 3 illustrates a calibration curve obtained by the ELISA according to the invention which is described in Example 3. In this Figure, the horizontal axis is for logarithm of the HT-3 activity and the perpendicular axis is for logarithm of optical density (OD) measure at the wave length of 450 nm.

The representative results are summarized in Table 1 below, and the calibration curve obtained by the above ELISA system comprising Mab-4B9-12-1 and Mab-3A5-6-1, is illustrated in FIG. 3. In this Figure, the horizontal axis is for logarithm of the HT-3 activity and the perpendicular axis is for logarithm of optical density (OD) measured at the wave length of 450 nm. As it is shown in FIG. 3, that ELISA system of the present invention enables the determination of the DPD activity over the range from about 2.5 to about 170 pmol/minute/ml. This high sensitivity of the DPD ELISA assay will be useful for determining the DPD level of biological samples from human body. Further the above DPD ELISA will thus enable to determine the DPD level of the samples from deficiency disease known to show rather a low level of DPD.

TABLE 1

| HT-3 activity* (pmol/minute/ml) | OD450** |
|---|---|
| 167.5 | 1.313 |
| 83.75 | 0.894 |
| 41.88 | 0.548 |
| 20.94 | 0.320 |
| 10.47 | 0.175 |
| 5.23 | 0.105 |
| 2.61 | 0.060 |

*HT-3 standard having the activity of 167.5 pmol/mg/minute was used.
**OD subtracted from the blank level.

EXAMPLE 4

Comparison Between the Results of the ELISA and the DPD Activity

The correlation between the level determined by the present ELISA method which was described in Example 3 and the level of enzymatic activity of DPD was investigated. The samples were breast cancer tissues and adjacent normal tissues which were surgical evulsions. The samples were prepared in the forms of tissue homogenates. Briefly, tumor and normal tissues were first homogenized in 10 mM Tris-HCl buffer (pH 7.4) containing 15 mM NaCl, 1.5 mM $MgCl_2$ and 50 µM potassium phosphate, and then centrifuged at 105000×g for 90 minutes. The supernatant was dialyzed overnight against 20 mM potassium phosphate buffer (pH 7.4) and 1 mM 2-mercaptoethanol.

The DPD activity was determined by a TLC plate method, close to that described by Fernandez-Salguero et al., 1995, Biochem. Pharm. 50, 1015–1020, wherein the sum of the 5-FU catabolites, i.e. dihydrofluorouracil, α-fluoro-β-ureidopropionate, and α-fluoro-β-alanine, formed from [6-$^{14}$C]5-FU was measured as described above. The ELISA was performed in the same manner as described in Example 3 by using a Scaber xenograft homogenate (105 pmol/minute/mg) as the standard.

Figure 4:
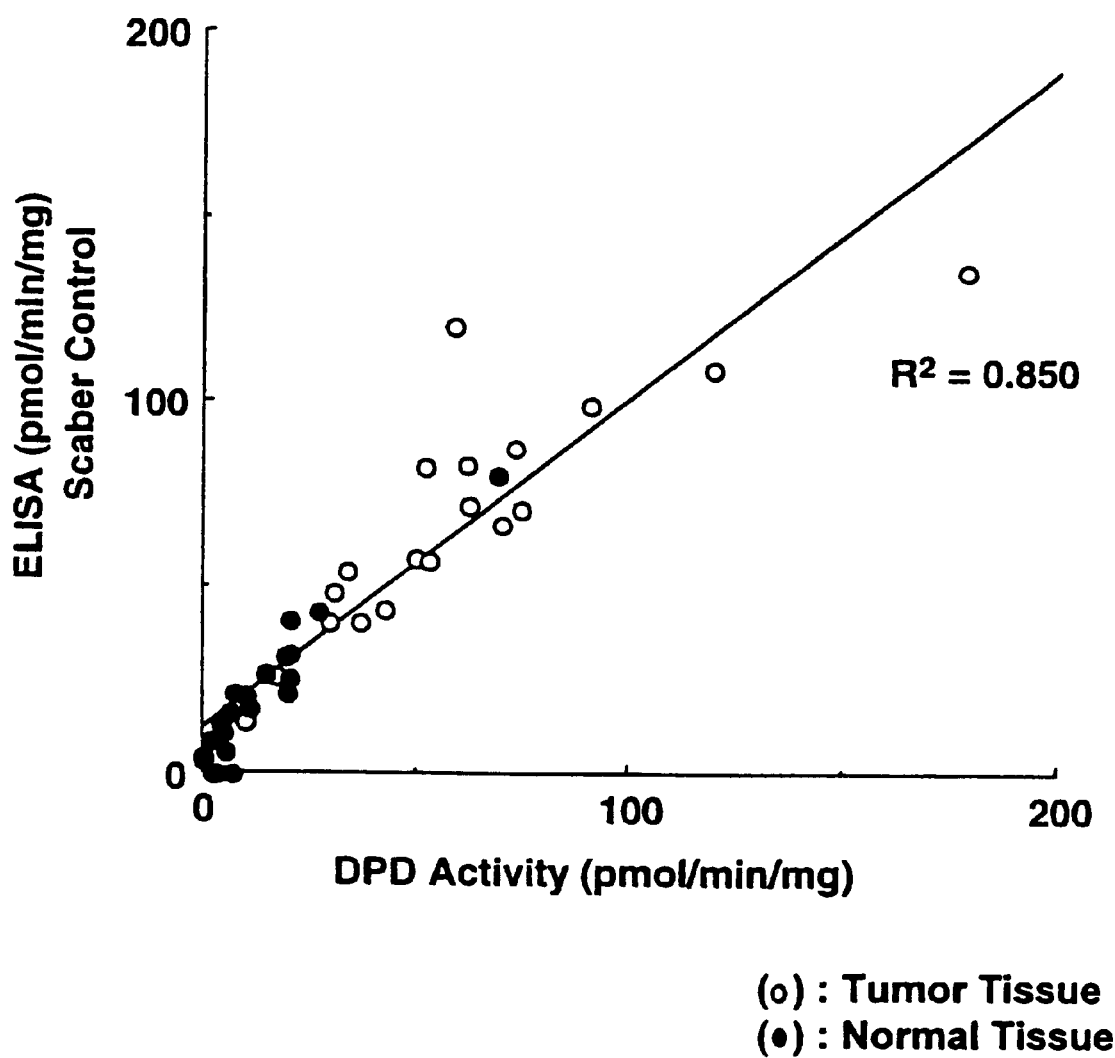
FIG. 4 illustrates the correlation between DPD levels detected by a DPD activity assay and the ELISA of the present invention in both normal tissues and tumor tissues of breast. The DPD activity assay is conducted by a conventional TLC method using $^{14}$C-radioactive label. The ELISA used here is that described in Example 3.

Each sample was assayed both by the above TLC plate method and by ELISA and the data of each sample was plotted on a graph of the vertical axis for the amount of DPD in pmol/minute/mg measured by ELISA and the horizontal axis for DPD activity measured by TLC method as shown in FIG. 4. High correlation between the results of the activity assay and the ELISA of the present invention was confirmed for both tumor tissues and normal tissues.

EXAMPLE 5

Application of the ELISA of the Invention to Measure the Efficacy of Antitumot Medicaments in the Series of 5-fluorouracil (5-FU) Derivatives, such as FURTULON One of the representatives of the antitumor medicaments in the series of 5-fluorouracil (5-FU) derivatives, namely FURTULON (5'-deoxy-5-fluorouridine (5'-dFUrd)) is a pro-drug which is converted into 5-FU by the action of pyrimidine nucleoside phosphorylase (PyNPase), i.e. thymidine phosphorylase in human cells.

A convenient assay system was devised for evaluating the ratio PyNPase/DPD in tumor tissues. That system comprises a combination of the ELISA system for the assay of PyNPase decribed by Nishida M. et al., 1996, Biol. Pharm. Bull. 19(11), 1407–1411, and the ELISA system of the invention described in the above Example 3.

To investigate whether the ratio PyNPase/DPD is a marker for the efficacy of FURTULON, that ratio was determined for a number of tumor tissues already known to be susceptible to FURTUILON and a number of tumor tissues already known to be refractory to FURTULON. The cell lines used as representative of the FURTULON-susceptible tissues are the following 9 human tumor xenograft cell lines: Scaber (squamous carcinoma, ATCC HTB-3), ZR-75 (breast carcinoma), MCF-7 (breast adenocarcinoma, ATCC HTB-22), LoVo (colorectal cancer, ATCC CCL-229), MKN45 (gastric cancer), SIHA (squamous carcinoma), ME-180 (epidermal carcinoma), HCT 116 (colorectal cancer) and COLO205 (colorectal cancer, ATCC CCL 222). The cell lines used as representative of the FURTULON-refractory tissues are the following 7 xenograft cell lines: SK-OV-3 (ovarian tumor, ATCC HTB-77), MAD-MB-231 (breast carcinoma), HT-29 (colorectal cancer, ATCC HTB-38), T-24 (bladder cancer, ATCC HTB-4), PC-3 (prostate adenocarcinoma), WiDr-1 (colorectal cancer, ATCC CCL-218) and MKN28 (gastric cancer).

Figure 5:
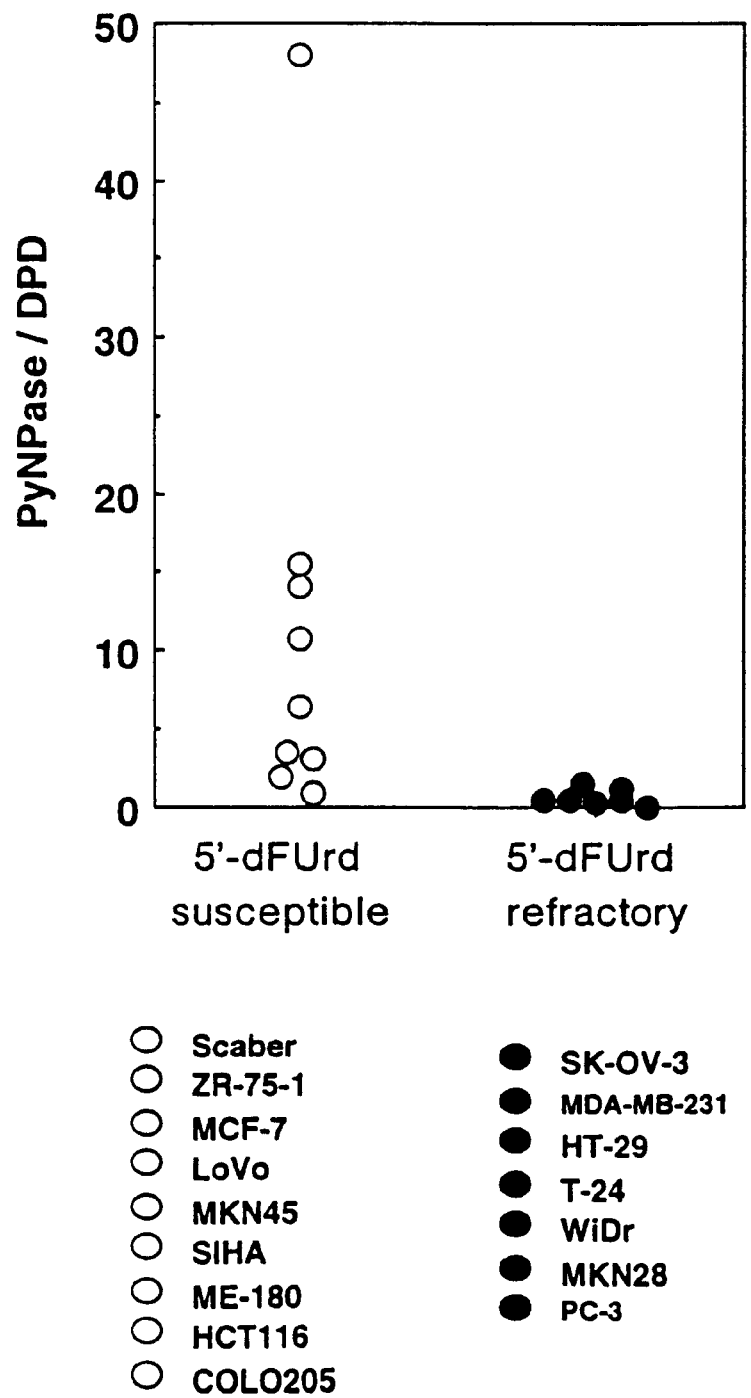
FIG. 5 illustrates the results of the study of the susceptibility to antitumor medicaments in the series of 5-fluorouracil (5-FU) derivatives, such as FURTULON, by determining PyNPase/DPD ratios as described in Example 5. PyNPase levels were assayed by using the method described by Nishida M. et al., 1996, Biol. Pharm. Bull. 19(11), 1407–1411. The ELISA used here is that described in Example 3.

The ratios determined based on the ELISA system of the present invention are plotted in the graph of FIG. 5. As it is shown in that Figure, the FURTULON-susceptible cell lines showed substantially higher PyNPase/DPD ratios than the refractory cell lines.

This result shows that the PyNPase/DPD ratio in tumor tissues is useful for measuring the efficacy of FURTULON in the treatment of patients suffering from tumor.

EXAMPLE 6

Immunoprecipitation Assay Using Monoclonal Antibodies According to the Invention A xenograft homogenate of tumor cell line, HT-3 was used as a biological sample which contained DPD. The xenograft homogenate (8.6 mg/ml) was treated through a protein G sepharose 4B column twice to absorb antibodies originating from the host, and was subjected to the following immunoprecipitation assay.

To the tubes containing 150 µl of HT-3 xenograft homogenate, 5 µg of monoclonal antibodies according to the invention to be tested were added and the tubes were incubated at for 4° C. for 2 hours. Then, each 20 µl of 50% Protein G-Sepharose 4B (Sigma, ST. Louis, Mo., USA) was added to the tube and the mixtures were further incubated at 4° C. for 2 hours. After the reaction, the mixtures were centrifuged to separate into bead fractions and supernatants. The collected bead fractions were washed with 20 mM sodium phosphate buffer (pH 7.0) five times, and eluted into 60 µl of 0.1M glycine-HCl buffer (pH 3.0); the eluates were neutralized with 3 µl of 1M Tris-HCl (pH 8.0) to obtain the preparation of the immunoprecipitates.

The samples of the supernatants and the eluates from the bead fractions, hereafter referred as bead eluates, were analyzed by SDS-PAGE and Western blotting.

FIG. 6 illustrates the results of the immunoprecipitation assay using the monoclonal antibodies of the present invention Mab-2B6-11-1, Mab-2E2-B3-1-3, Mab-4B9-12-1 and Mab-9C7-30-1.

FIGS. 6-1(*a*) and (*b*) show the electrophoretic pattern of SDS-PAGE, where (*a*) is for the supernatants and (*b*) is the bead eluates of the immunoprecipitates, the bands being visualized by silver staining (2D-silver stain Daiichi, Daiichi Pure Chemicals, Tokyo, Japan).

FIGS. 6-2(*a*), (*b*) and (*c*) show a results of Western blotting, where (*a*) is the result obtained from the supernatant detected using anti DPD-1 polypeptide antibody, (*b*) is the result from the bead eluates from the immunoprecipitates detected by using anti DPD-1 polypeptide antibody, and (*c*) show the result from the same bead eluates as (*b*) in which the monoclonal antibody 3A5-6-1 of the present invention was used for the detection. The respective lanes correspond to the results of the immunoprecipitation assay using the following samples: lane 1: mouse IgG 1; lane 2: 2B6-11-1; lane 3: 2E2-B3-1-3; lane :4B9-12-1; and lane 5: 9C7-30-1.

The lane c in FIG. 6-2(*b*) is the run of homogenate of HT-3 as a positive control.

As shown in FIG. 6-1(*b*), the immunoprecipitation was observed as the bands corresponding to about 120 kDa in the cases of the monoclonal antibodies of the present invention, Mab-2E2-B3-1-3 (lane 3), and Mab-4B9-12-1 (lane 4). On the PAGE gel, the bands seen around 50 kDa and 25 kDa correspond to the heavy chain and light chain of the antibodies utilized.

At the same time, Western blotting was carried out using the supernatant and the bead eluate. Either rabbit anti-DPD peptide-1 antibody or Mab-3A5-6-1 was utilized for the detection of DPD. As it is shown in FIG. 6-1(*a*), the band corresponding to DPD was not observed in the samples of the supernatant (see lanes 3 and 4), while the single bands around 120 kDa were observed using anti-DPD peptide-1 antibody or Mab-3A5-6-1 in the samples which were eluted from the beads resulted from the immuno precipitation with Mab4B9-12-1 and Mab-2E2-B3-1-3 as show in FIG. 6-2(*b*) and (*c*), which evidenced that the single band observed near 120 kDa on SDS-PAGE corresponded to DPD. Further, the DPD activities in the samples of the bead eluates from the immuno precipitates with Mab-4B9-12-1 and the corresponding supernatant were assayed, and the DPD activity was observed only in the bead eluates from the immunoprecipitates as shown in Table 2 below:

TABLE 2

| [DPD activity: pmol/minute/ml] HT-3 homogenate/Mab + beads | | |
|---|---|---|
| Antibody added | Supernatants | Bead eluates |
| Mouse IgG1 | 118.2 | <1.41 |
| 4B9-12-1 | <1.41 | 85.3 |

These results show that the monoclonal antibodies of the present invention, i.e. Mab-4B9-12-1 and Mab-2E2-B3-1-3 recognize the active DPD molecule having the native conformation and that the specificity of these antibodies to DPD is very high as their immunoprecipitates are observed as single bands.

Moreover, it was confirmed that Mab-3A5-6-1 specifically recognizes the DPD molecule which was also specifically recognized by Mab-4B9-12-1, this ensures the reliability of the sandwich ELISA system using these monoclonal antibodies of the present invention.

As the skilled person will readily understand, monoclonal antibodies according to the present invention are also useful for the preparation of an affinity column for the purification of DPD.

What is claimed is:

1. A monoclonal antibody which can be produced by a hybridoma cell line selected from the group consisting of hybridoma cell lines 3A5-6-1 (FERM BP-6015), 4B9-12-1 (FERM BP-6016), and 2E2-B3-1-3 (FERM BP-6014).

2. monoclonal antibody of claim 1 which crossreacts with a monoclonal antibody produced from a hybridoma cell line selected from the group consisting of hybridoma cells lines 3A5-6-1 (FERM BP-6015), 4B9-12-1 (FERM BP-6016), and 2E2-B3-1-3 (FERM BP-6014).

3. A hybridoma line which is selected from the group consisting of hybridoma cell lines 3A5-6-1 (FERM BP-6015), 4B9-12-1 (FERM BP-6016), and 2E2-B3-1-3 (FERM BP-6014).

4. A kit for the detection or determination of the amount of dihydropyrimidine dehydrogenase in a biological sample which comprises:

(a) a monoclonal antibody which can be produced from a hybridoma cell line selected from the group consisting of hybridoma cell lines 3A5-6-1 (FERM BP-6015), 4B9-12-1 (FERM BP-6016), and 2E2-B3-1-3 (FERM BP-6014); and (b) a label for qualitatively or quantitatively detecting an immunoconjugate of the at least one monoclonal antibody and dihydropyrimidine dehydrogenase.

* * * * *

SEQUENCE LISTING

<160> NUMBER OF SEQ ID NOS: 8

<210> SEQ ID NO 1
<211> LENGTH: 3951
<212> TYPE: DNA
<213> ORGANISM: Homo sapiens

<400> SEQUENCE: 1
gctgtcactt ggctctctgg ctggagcttg aggacgcaag gagggtttgt cactggcaga     60
ctcgagactg taggcactgc catggcccct gtgctcagta aggactcggc ggacatcgag    120

-continued

```
agtatcctgg ctttaaatcc tcgaacacaa actcatgcaa ctctgtgttc cacttcggcc       180
aagaaattag acaagaaaca ttggaaaaga atcctgata agaactgctt taattgtgag       240
aagctggaga ataattttga tgacatcaag cacacgactc ttggtgagcg aggagctctc      300
cgagaagcaa tgagatgcct gaaatgtgca gatgcccgt gtcagaagag ctgtccaact       360
aatcttgata ttaaatcatt catcacaagt attgcaaaca gaactatta tggagctgct      420 aagatgatat tttctgacaa cccacttggt ctgacttgtg aatggtatg tccaacctct     480 gatctatgtg taggtggatg caatttatat gccactgaag agggacccat taatattggt   540
ggattgcagc aatttgctac tgaggtattc aaagcaatga gtatcccaca gatcagaaat   600
ccttcgctgc ctcccccaga aaaatgtct gaagcctatt ctgcaaagat tgctcttttt    660
ggtgctgggc ctgcaagtat aagttgtgct ccttttttgg ctcgattggg gtactctgac   720
atcactatat ttgaaaaaca agaatatgtt ggtggtttaa gtacttctga aattcctcag   780
ttccggctgc cgtatgatgt agtgaatttt gagattgagc taatgaagga ccttggtgta   840
aagataattt gcggtaaaag cctttcagtg aatgaaatga ctcttagcac tttgaaagaa   900
aaaggctaca agctgctttt cattggaata ggtttgccag aacccaataa agatgccatc   960
ttccaaggcc tgacgcagga ccaggggttt tatacatcca aagactttt gccacttgta   1020 gccaaaggca gtaaagcagg aatgtgcgcc tgtcactctc cattgccatc gatacgggga   1080
gtcgtgattg tacttggagc tggagacact gccttcgact gtgcaacatc tgctctacgt   1140
tgtggagctc gccgagtgtt catcgtcttc agaaaaggct ttgttaatat aagagctgtc   1200
cctgaggaga tggagcttgc taaggaagaa aagtgtgaat ttctgccatt cctgtccccca  1260 cggaaggtta tagtaaaagg tgggagaatt gttgctatgc agtttgttcg acagagcaa   1320 gatgaaactg gaaaatggaa tgaagatgaa gatcagatgg tccatctgaa agccgatgtg  1380
gtcatcagtg cctttggttc agttctgagt gatcctaaag taaaagaagc cttgagccct  1440
ataaaattta acagatgggg tctcccagaa gtagatccag aaactatgca aactagtgaa  1500
gcatgggtat ttgcaggtgg tgatgtcgtt ggtttggcta cactacagt ggaatcggtg  1560 aatgatggaa agcaagcttc ttggtacatt cacaaatacg tacagtcaca atatggagct  1620
tccgtttctg ccaagcctga actaccctc ttttacactc ctattgatct ggtggacatt    1680
agtgtagaaa tggccggatt gaagtttata atccttttg gtcttgctag cgcaactcca    1740
gccaccagca catcaatgat tcgaagagct tttgaagctg atgggtttt tgccctcacc    1800 aaaactttct ctcttgataa ggacattgtg acaaatgttt ccccccagaat catccgggga  1860 accacctctg gccccatgta tggccctgga caaagctcct ttctgaatat tgagctcatc   1920
agtgagaaaa cggctgcata ttggtgtcaa agtgtcactg aactaaaggc tgacttccca  1980
gacaacattg tgattgctag cattatgtgc agttacaata aaaatgactg gacggaactt  2040
gccaagaagt ctgaggattc tggagcagat gccctggagt taaatttatc atgtccacat  2100
ggcatgggag aaagaggaat gggcctggcc tgtgggcagg atccagagct ggtgcggaac  2160
atctgccgct gggttaggca agctgttcag attccttttt ttgccaagct gaccccaaat   2220
gtcactgata ttgtgagcat cgcaagagct gcaaggaag gtggtgccaa tggcgttaca   2280
gccaccaaca ctgtctcagg tctgatggga ttaaaatctg atggcacacc ttggccagca   2340
gtggggattg caaagcgaac tacatatgga ggagtgtctg gacagcaat cagacctatt    2400 gctttgagag ctgtgacctc cattgctcgt gctctgcctg gatttcccat tttggctact   2460
```

-continued

```
ggtggaattg actctgctga aagtggtctt cagtttctcc atagtggtgc ttccgtcctc    2520
caggtatgca gtgccattca gaatcaggat ttcactgtga tcgaagacta ctgcactggc    2580
ctcaaagccc tgctttatct gaaaagcatt gaagaactac aagactggga tggacagagt    2640
ccagctactg tgagtcacca gaaagggaaa ccagttccac gtatagctga actcatggac    2700
aagaaactgc caagttttgg accttatctg gaacagcgca agaaaatcat agcagaaaac    2760
aagattagac tgaaagaaca aaatgtagct ttttcaccac ttaagagaag ctgttttatc    2820
cccaaaaggc ctattcctac catcaaggat gtaataggaa aagcactgca gtaccttgga    2880
acatttggtg aattgagcaa cgtagagcaa gttgtggcta tgattgatga agaaatgtgt    2940
atcaactgtg gtaaatgcta catgacctgt aatgattctg ctaccaggc tatacagttt     3000 gatccagaaa cccacctgcc caccataacc gacacttgta caggctgtac tctgtgtctc    3060
agtgtttgcc ctattgtcga ctgcatcaaa atggtttcca ggacaacacc ttatgaacca    3120
aagagaggcg taccttatc tgtgaatccg gtgtgttaag gtgatttgtg aaacagttgc     3180
tgtgaacttt catgtcacct acatatgctg atctcttaaa atcatgatcc ttgtgttcag    3240
ctctttccaa attaaaacaa atatacattt tctaaataaa aatatgtaat ttcaaaatac    3300
atttgtaagt gtaaaaaatg tctcatgtca atgaccattc aattagtggc ataaaataga    3360
ataattcttt tctgaggata gtagttaaat aactgtgtgg cagttaattg gatgttcact    3420
gccagttgtc ttatgtgaaa aattaacttt tgtgtggca attagtgtga cagtttccaa     3480
attgccctat gctgtgctcc atatttgatt tctaattgta agtgaaatta agcattttga    3540
aacaaagtac tctttaacat acaagaaaat gtatccaagg aaacatttta tcaataaaaa    3600
ttacctttaa ttttaatgct gtttctaaga aaatgtagtt agctccataa agtacaaatg    3660
aagaaagtca aaattatttt gctatggcag gataagaaag cctaaaattg agtttgtgga    3720
ctttattaag taaaatcccc ttcgctgaaa ttgcttatttt ttggtgttgg atagaggata   3780
gggagaatat ttactaacta aataccattc actactcatg cgtgagatgg gtgtacaaac    3840
tcatcctctt ttaatggcat ttctctttaa actatgttcc taaccaaatg agatgatagg    3900
atagatcctg gttaccactc ttttactgtg cacatatggg ccccggaatt c             3951
```

<210> SEQ ID NO 2
<211> LENGTH: 1025
<212> TYPE: PRT
<213> ORGANISM: Homo sapiens

<400> SEQUENCE: 2

```
Met Ala Pro Val Leu Ser Lys Asp Ser Ala Asp Ile Glu Ser Ile Leu
 1               5                  10                  15

Ala Leu Asn Pro Arg Thr Gln Thr His Ala Thr Leu Cys Ser Thr Ser
            20                  25                  30

Ala Lys Lys Leu Asp Lys Lys His Trp Lys Arg Asn Pro Asp Lys Asn
        35                  40                  45

Cys Phe Asn Cys Glu Lys Leu Glu Asn Asn Phe Asp Asp Ile Lys His
    50                  55                  60

Thr Thr Leu Gly Glu Arg Gly Ala Leu Arg Glu Ala Met Arg Cys Leu
65                  70                  75                  80

Lys Cys Ala Asp Ala Pro Cys Gln Lys Ser Cys Pro Thr Asn Leu Asp
                85                  90                  95

Ile Lys Ser Phe Ile Thr Ser Ile Ala Asn Lys Asn Tyr Tyr Gly Ala
            100                 105                 110
```

-continued

```
Ala Lys Met Ile Phe Ser Asp Asn Pro Leu Gly Leu Thr Cys Gly Met
        115                 120                 125
Val Cys Pro Thr Ser Asp Leu Cys Val Gly Cys Asn Leu Tyr Ala
        130                 135             140
Thr Glu Gly Pro Ile Asn Ile Gly Gly Leu Gln Gln Phe Ala Thr
145                 150                 155                 160
Glu Val Phe Lys Ala Met Ser Ile Pro Gln Ile Arg Asn Pro Ser Leu
            165                 170                 175
Pro Pro Pro Glu Lys Met Ser Glu Ala Tyr Ser Ala Lys Ile Ala Leu
                180                 185                 190
Phe Gly Ala Gly Pro Ala Ser Ile Ser Cys Ala Ser Phe Leu Ala Arg
        195                 200                 205
Leu Gly Tyr Ser Asp Ile Thr Ile Phe Glu Lys Gln Glu Tyr Val Gly
        210                 215                 220
Gly Leu Ser Thr Ser Glu Ile Pro Gln Phe Arg Leu Pro Tyr Asp Val
225                 230                 235                 240
Val Asn Phe Glu Ile Glu Leu Met Lys Asp Leu Gly Val Lys Ile Ile
            245                 250                 255
Cys Gly Lys Ser Leu Ser Val Asn Glu Met Thr Leu Ser Thr Leu Lys
            260                 265                 270
Glu Lys Gly Tyr Lys Ala Ala Phe Ile Gly Ile Gly Leu Pro Glu Pro
        275                 280                 285
Asn Lys Asp Ala Ile Phe Gln Gly Leu Thr Gln Asp Gln Gly Phe Tyr
        290                 295                 300
Thr Ser Lys Asp Phe Leu Pro Leu Val Ala Lys Gly Ser Lys Ala Gly
305                 310                 315                 320
Met Cys Ala Cys His Ser Pro Leu Pro Ser Ile Arg Gly Val Val Ile
                325                 330                 335
Val Leu Gly Ala Gly Asp Thr Ala Phe Asp Cys Ala Thr Ser Ala Leu
            340                 345                 350
Arg Cys Gly Ala Arg Arg Val Phe Ile Val Phe Arg Lys Gly Phe Val
        355                 360                 365
Asn Ile Arg Ala Val Pro Glu Glu Met Glu Leu Ala Lys Glu Glu Lys
370                 375                 380
Cys Glu Phe Leu Pro Phe Leu Ser Pro Arg Lys Val Ile Val Lys Gly
385                 390                 395                 400
Gly Arg Ile Val Ala Met Gln Phe Val Arg Thr Glu Gln Asp Glu Thr
            405                 410                 415
Gly Lys Trp Asn Glu Asp Glu Asp Gln Met Val His Leu Lys Ala Asp
        420                 425                 430
Val Val Ile Ser Ala Phe Gly Ser Val Leu Ser Asp Pro Lys Val Lys
        435                 440                 445
Glu Ala Leu Ser Pro Ile Lys Phe Asn Arg Trp Gly Leu Pro Glu Val
        450                 455                 460
Asp Pro Glu Thr Met Gln Thr Ser Glu Ala Trp Val Phe Ala Gly Gly
465                 470                 475                 480
Asp Val Val Gly Leu Ala Asn Thr Thr Val Glu Ser Val Asn Asp Gly
            485                 490                 495
Lys Gln Ala Ser Trp Tyr Ile His Lys Tyr Val Gln Ser Gln Tyr Gly
            500                 505                 510
Ala Ser Val Ser Ala Lys Pro Glu Leu Pro Leu Phe Tyr Thr Pro Ile
        515                 520                 525
Asp Leu Val Asp Ile Ser Val Glu Met Ala Gly Leu Lys Phe Ile Asn
```

-continued

```
        530                 535                 540
Pro Phe Gly Leu Ala Ser Ala Thr Pro Ala Thr Ser Thr Ser Met Ile
545                 550                 555                 560
Arg Arg Ala Phe Glu Ala Gly Trp Gly Phe Ala Leu Thr Lys Thr Phe
                565                 570                 575
Ser Leu Asp Lys Asp Ile Val Thr Asn Val Ser Pro Arg Ile Ile Arg
                580                 585                 590
Gly Thr Thr Ser Gly Pro Met Tyr Gly Pro Gly Gln Ser Ser Phe Leu
                595                 600                 605
Asn Ile Glu Leu Ile Ser Glu Lys Thr Ala Ala Tyr Trp Cys Gln Ser
                610                 615                 620
Val Thr Glu Leu Lys Ala Asp Phe Pro Asp Asn Ile Val Ile Ala Ser
625                 630                 635                 640
Ile Met Cys Ser Tyr Asn Lys Asn Asp Trp Thr Glu Leu Ala Lys Lys
                645                 650                 655
Ser Glu Asp Ser Gly Ala Asp Ala Leu Glu Leu Asn Leu Ser Cys Pro
                660                 665                 670
His Gly Met Gly Glu Arg Gly Met Gly Leu Ala Cys Gly Gln Asp Pro
                675                 680                 685
Glu Leu Val Arg Asn Ile Cys Arg Trp Val Arg Gln Ala Val Gln Ile
                690                 695                 700
Pro Phe Phe Ala Lys Leu Thr Pro Asn Val Thr Asp Ile Val Ser Ile
705                 710                 715                 720
Ala Arg Ala Ala Lys Glu Gly Gly Ala Asn Gly Val Thr Ala Thr Asn
                725                 730                 735
Thr Val Ser Gly Leu Met Gly Leu Lys Ser Asp Gly Thr Pro Trp Pro
                740                 745                 750
Ala Val Gly Ile Ala Lys Arg Thr Thr Tyr Gly Gly Val Ser Gly Thr
                755                 760                 765
Ala Ile Arg Pro Ile Ala Leu Arg Ala Val Thr Ser Ile Ala Arg Ala
770                 775                 780
Leu Pro Gly Phe Pro Ile Leu Ala Thr Gly Gly Ile Asp Ser Ala Glu
785                 790                 795                 800
Ser Gly Leu Gln Phe Leu His Ser Gly Ala Ser Val Leu Gln Val Cys
                805                 810                 815
Ser Ala Ile Gln Asn Gln Asp Phe Thr Val Ile Glu Asp Tyr Cys Thr
                820                 825                 830
Gly Leu Lys Ala Leu Leu Tyr Leu Lys Ser Ile Glu Glu Leu Gln Asp
                835                 840                 845
Trp Asp Gly Gln Ser Pro Ala Thr Val Ser His Gln Lys Gly Lys Pro
                850                 855                 860
Val Pro Arg Ile Ala Glu Leu Met Asp Lys Lys Leu Pro Ser Phe Gly
865                 870                 875                 880
Pro Tyr Leu Glu Gln Arg Lys Lys Ile Ile Ala Glu Asn Lys Ile Arg
                885                 890                 895
Leu Lys Glu Gln Asn Val Ala Phe Ser Pro Leu Lys Arg Ser Cys Phe
                900                 905                 910
Ile Pro Lys Arg Pro Ile Pro Thr Ile Lys Asp Val Ile Gly Lys Ala
                915                 920                 925
Leu Gln Tyr Leu Gly Thr Phe Gly Glu Leu Ser Asn Val Glu Gln Val
                930                 935                 940
Val Ala Met Ile Asp Glu Glu Met Cys Ile Asn Cys Gly Lys Cys Tyr
945                 950                 955                 960
```

```
Met Thr Cys Asn Asp Ser Gly Tyr Gln Ala Ile Gln Phe Asp Pro Glu
                965                 970                 975

Thr His Leu Pro Thr Ile Thr Asp Thr Cys Thr Gly Cys Thr Leu Cys
            980                 985                 990

Leu Ser Val Cys Pro Ile Val Asp Cys Ile Lys Met Val Ser Arg Thr
        995                1000                1005

Thr Pro Tyr Glu Pro Lys Arg Gly Val Pro Leu Ser Val Asn Pro Val
    1010                1015                1020

Cys
1025

<210> SEQ ID NO 3
<211> LENGTH: 25
<212> TYPE: DNA
<213> ORGANISM: Artificial Sequence
<220> FEATURE:
<223> OTHER INFORMATION: Description of Artificial Sequence:Cloned
      segment of DPD gene, corresponding to nucleotides 1770-1785
      of SEQ ID No: 1, with Eco RI Linker at 5' end

<400> SEQUENCE: 3
cgcgaattct tttgaagctg gatgg                                          25

<210> SEQ ID NO 4
<211> LENGTH: 26
<212> TYPE: DNA
<213> ORGANISM: Artificial Sequence
<220> FEATURE:
<223> OTHER INFORMATION: Description of Artificial Sequence:26 mer
      sequence corresponding to negative strand complementary to
      3148-3164 of SEQ ID NO: 1, with Eco RI linker at 5' end

<400> SEQUENCE: 4
cgcgaattct caccttaaca caccgg                                         26

<210> SEQ ID NO 5
<211> LENGTH: 16
<212> TYPE: DNA
<213> ORGANISM: Artificial Sequence
<220> FEATURE:
<223> OTHER INFORMATION: Description of Artificial Sequence:16 mer
      negative strand complementary to nucleotides 3495-3510 of
      SEQ ID NO: 1

<400> SEQUENCE: 5
aatcaaatat ggagca                                                    16

<210> SEQ ID NO 6
<211> LENGTH: 18
<212> TYPE: PRT
<213> ORGANISM: Artificial Sequence
<220> FEATURE:
<223> OTHER INFORMATION: Description of Artificial Sequence: Synthetic
      sequence corresponding to residues 52-69 of Seq ID NO: 2

<400> SEQUENCE: 6

Cys Glu Lys Leu Glu Asn Asn Phe Asp Asp Ile Lys His Thr Thr Leu
  1               5                  10                  15

Gly Glu

<210> SEQ ID NO 7
<211> LENGTH: 20
<212> TYPE: PRT
<213> ORGANISM: Artificial Sequence
```

```
<220> FEATURE:
<223> OTHER INFORMATION: Description of Artificial Sequence:Syntesized
      based on sequence described in SEQ ID NO: 2 and corresponding to
      660-679

<400> SEQUENCE: 7

Ser Gly Ala Asp Ala Leu Glu Leu Asn Leu Ser Cys Pro His Gly Met
 1               5                  10                  15

Gly Glu Arg Gly
            20

<210> SEQ ID NO 8
<211> LENGTH: 26
<212> TYPE: DNA
<213> ORGANISM: Artificial Sequence
<220> FEATURE:
<223> OTHER INFORMATION: Description of Artificial Sequence:Eco RI
      linker attached to 5' end of cloned sequence corresponding to
      nucleotides 62-78 of SEQ ID NO: 1

<400> SEQUENCE: 8
cgcgaattct cgagactgta ggcact                                        26
```